US008288526B2

(12) United States Patent
Torii et al.

(10) Patent No.: US 8,288,526 B2
(45) Date of Patent: *Oct. 16, 2012

(54) INOSINE DERIVATIVES AND PRODUCTION METHODS THEREFOR

(75) Inventors: Takayoshi Torii, Kawasaki (JP); Kunisuke Izawa, Kawasaki (JP); Doo Ok Jang, Wonju-si (KR); Dae Hyan Cho, Suwon (KR)

(73) Assignee: Ajinomoto Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/847,399

(22) Filed: Jul. 30, 2010

(65) Prior Publication Data

US 2011/0028706 A1 Feb. 3, 2011

Related U.S. Application Data

(63) Continuation of application No. 11/304,675, which is a continuation of application No. PCT/JP2004/008783, filed on Jun. 16, 2004, now Pat. No. 7,816,513.

(30) Foreign Application Priority Data

Jun. 16, 2003 (JP) ................................. 2003-170361

(51) Int. Cl.
C07H 19/173 (2006.01)
C07H 19/167 (2006.01)
C07H 19/16 (2006.01)

(52) U.S. Cl. ................... 536/27.8; 536/27.21; 536/27.1; 514/45; 544/265

(58) Field of Classification Search ............... 536/27.8, 536/27.21, 27.1; 514/45; 544/265
See application file for complete search history.

(56) References Cited

U.S. PATENT DOCUMENTS 5,604,209 A 2/1997 Ubasawa et al.

FOREIGN PATENT DOCUMENTS

| EP | 0 493 602 | 7/1992 |
| JP | 03-240795 | 10/1991 |
| WO | WO 92/02516 | 2/1992 |
| WO | WO 93/06119 | 4/1993 |

OTHER PUBLICATIONS

C.K. Chu. et al., "General Syntheses of 2',3'-Dideoxynucleosides and 2',3'-Didehydro-2',3'-Dideoxynucleosides", J. Org. Chem., vol. 54, No. 9, 1989, pp. 2217-2225.

F.A. Luzzio, et al , "A Facile Route to Pyrimidine-Base Nucleoside Olefins: Application to the Synthesis of D4T (Stavudine)1". J. Org. Chem., vol. 59, No. 24, 1994, pp. 7267-7272.

D.H.R. Barton, et al., "Towards Dideoxynucleosides: The Silicon Approach", Tetrahedron Letters, vol. 32, No. 23, 1991, pp. 2569-2572.

D.H.R. Barton, et al., "Hypophosphorous Acid and its Salts: New Reagents for Radical Chain Deoxygenation, Dehalogenation and Deamination", Tetrahedron Letters, vol. 33, No. 39, 1992, pp. 5709-5712.

S. Takamatsu, et al., "Radical Deoxygenation and Dehalogenation of Nucleoside Derivatives With Hypophosphorous Acid and Dialkyl Phosphites", Tetrahedron Letters, vol. 42, 2001, pp. 7605-7608.

Narayan C. Bar, et al. Tetrahedron, vol. 53, No. 13. pp. 4727-4738, 1997.

David C. Johnson II and Theodore S. Widlanski, Organic Letters 2004 vol. 6, No. 25 pp. 4643-4646.

Japanese Office Action issued on Aug. 20, 2012 in patent application No. 2010-183680 (with English Translation).

*Primary Examiner* — Shaojia Anna Jiang
*Assistant Examiner* — Michael C Henry
(74) *Attorney, Agent, or Firm* — Oblon, Spivak, McClelland, Maier & Neustadt, L.L.P.

(57) ABSTRACT

The present invention provides a method for producing an inosine derivative represented by the following general formula (1) including the steps of subjecting an inosine derivative of general formula (3) to dithiocarbonylation and carrying out radical reduction of the obtained compound. According to the present invention there can be produced compounds useful as anti-AIDS drugs on industrial scale.

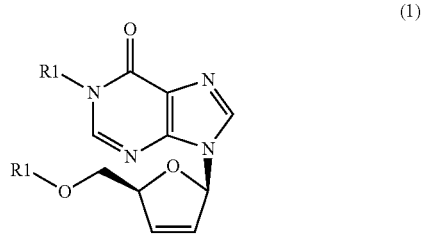

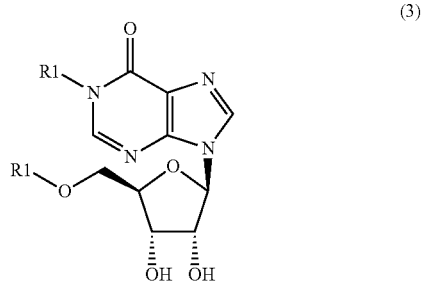

wherein R1 may be the same or different and are each benzyl group, benzhydryl group or trityl group, each of which may have a substituent in general formulas (1) and (3).

6 Claims, No Drawings

INOSINE DERIVATIVES AND PRODUCTION METHODS THEREFOR

CROSS REFERENCES TO RELATED APPLICATIONS

This application is a continuation of U.S. patent application Ser. No. 11/304,675, filed on Dec. 16, 2005, now U.S. Pat. No. 7,816,513, which was a continuation of International Patent Application No. PCT/JP2004/008783, filed on Jun. 16, 2004, and claims priority to Japanese Patent Application No. 2003-170361, filed on Jun. 16, 2003.

BACKGROUND OF THE INVENTION

The present invention relates to methods for producing 2',3'-dideoxyinosine useful as an antiviral agent, represented by the following formula (7), (which is called didanosine (DDI) and hereinafter referred to as "DDI"), intermediate compounds that are essential in producing the DDI, and methods for producing the intermediate compounds.

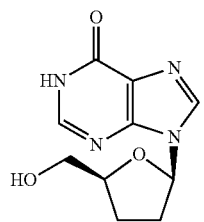
(7)

DDI is useful as an antiviral agent and has already been approved as an anti-AIDS drug in many countries including the U.S.A., Japan and European countries.

To obtain a dideoxy (DD) derivative from nucleoside, there is conventionally known, for example, a method where hydroxyl groups at the 2'- and 3'-positions of nucleoside are subjected to thiocarbonylation, followed by radical reduction to form a didehydrodideoxy (D4) derivative, and the D4 derivative is subjected to hydrogenation or the like, thereby obtaining a dideoxy (DD). Some synthesis methods for various antiviral agents based on the above-mentioned technique are reported, which include a method described in: Chu, C. K. et. al. J. Org. Chem. 1989, 54, 2217-2225. However, the method described in the aforementioned literature requires a step of protecting a hydroxyl group at the 5'-position of the nucleoside in advance. For example, when adenosine is used as a raw material for the production of the DD derivative, tert-butyldimethylsilyl group (e.g., refer to Chu, C. K. et. al. J. Org. Chem. 1989. 54, 2217-2225) and trityl group (e.g., refer to Yurkevich, A. M. et al. Tetrahedron, 1969, 25, 477-484) are adopted as the protective groups. However, when DDI is produced using inosine as a raw material, the aforementioned protective groups cause the problems shown below. Namely, as for the tert-butyldimethylsilyl group, it is expensive and a fluorine-based reagent becomes necessary in the process of deprotection. The use of trityl group prevents the progress of the reaction with satisfactory yields (e.g., refer to Japanese Patent Unexamined Publication (JP Kokai) Hei 07-109290). In light of the above, there is an increasing demand for development of methods for producing DDI (7) and 2',3'-didehydro-2',3'-dideoxyinosine (4) (which is called D4 inosine and hereinafter referred to as "D4I") inexpensively so as to obtain satisfactory yields.

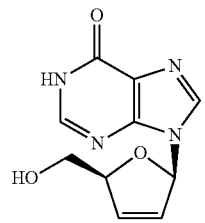
(4)

There is known a compound where amino group and hydroxyl group respectively at the 1-position and the 5'-position of inosine are protected by benzyl (e.g., Luzzio, F. A. et al. J. Org. Chem., 1994, 59, 7267-7272). However, nothing has been known about a production method for the DDI from the above-mentioned compound as a raw material by subjecting two hydroxyl groups at the 2'- and 3'-positions to deoxylation.

DISCLOSURE OF INVENTION

Objects of the present invention are to provide methods for producing DDI (7), D4I (4) and derivatives thereof in good yields.

After intensive researches and studies, the inventors of the present invention newly found that an inosine derivative represented by the following general formula (1) can be derived from 5'-O-benzyl-N$^1$-benzylinosine derivative that has been synthesized in accordance with a method, for example, as described in Luzzio, F. A. et al. J. Org. Chem., 1994, 59, 7267-7272, by subjecting the raw material to thiocarbonylation of hydroxyl groups at the 2'- and 3'-positions and subsequently carrying out radical reduction. The present invention has been accomplished based on the above-mentioned finding. Namely, the present invention provides a method for producing an inosine derivative represented by the following general formula (1),

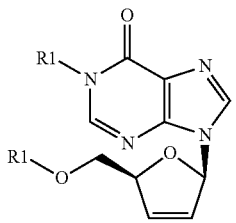
(1)

comprising the steps of subjecting an inosine derivative of the following general formula (3) to dithiocarbonylation to obtain a compound, and subjecting the obtained compound to radical reduction:

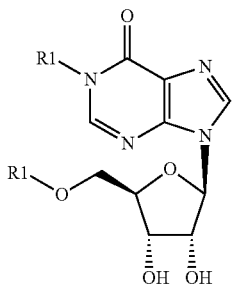
(3)

wherein R1 may be the same or different and are each benzyl group, benzhydryl group or trityl group, each of which may have a substituent in general formula (1) and (3).

Also, the present invention provides a method for producing an inosine derivative represented by the following general formula (2), comprising the step of hydrogenating the inosine derivative represented by the above-mentioned general formula (1):

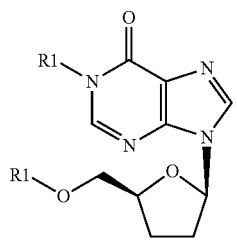

(2)

wherein R1 may be the same or different and are each benzyl group, benzhydryl group or trityl group, each of which may have a substituent.

The present invention also provides a method for producing 2',3'-dideoxyinosine (DDI), characterized by hydrogenating the inosine derivative represented by the above-mentioned general formula (1) or the inosine derivative represented by the above-mentioned general formula (2).

In addition, the present invention provides a method for producing 2',3'-didehydro-2',3'-dideoxyinosine (D4I) represented by the above-mentioned general formula (4), comprising the step of eliminating substituents R1 from the inosine derivative represented by the above-mentioned general formula (1).

Further, the present invention provides a method for producing 2',3'-dideoxyinosine (DDI), comprising the steps of:

subjecting the inosine derivative represented by the above-mentioned general formula (3) to dithiocarbonylation to obtain a compound of the following general formula (5):

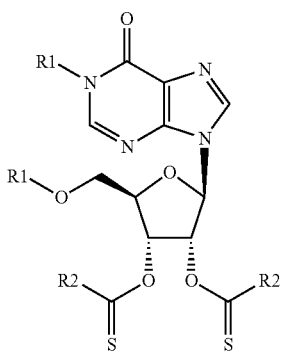

(5)

wherein R1 may be the same or different and are each benzyl group, benzhydryl group or trityl group, each of which may have a substituent; and R2 are each an alkylthio group having 1 to 12 carbon atoms, an alkoxyl group having 1 to 12 carbon atoms or an alkylamino group having 1 to 12 carbon atoms;

subjecting the compound of the general formula (5) to radical reduction to obtain the inosine derivative represented by the above-mentioned general formula (1);

hydrogenating the inosine derivative represented by the general formula (1) to obtain the compound represented by the above-mentioned general formula (2); and eliminating the substituents R1 from the compound represented by the general formula (2).

Also, the present invention provides a method for producing 2',3'-didehydro-2',3'-dideoxyinosine (D4I) represented by the above-mentioned general formula (4), comprising the steps of:

subjecting the inosine derivative represented by the above-mentioned general formula (3) to dithiocarbonylation to obtain the compound of the above-mentioned general formula (5);

eliminating the substituents R1 from the compound represented by the general formula (5) to obtain a compound of the following general formula (6):

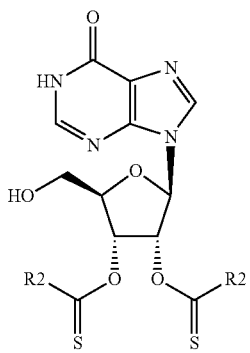

(6)

wherein R2 are each an alkylthio group having 1 to 12 carbon atoms, an alkoxyl group having 1 to 12 carbon atoms or an alkylamino group having 1 to 12 carbon atoms; and subjecting the compound of the general formula (6) to radical reduction.

Also, the present invention provides a method for producing 2',3'-didehydro-2',3'-dideoxyinosine (D4I) represented by the above-mentioned general formula (4), comprising the steps of subjecting the inosine derivative represented by the above-mentioned general formula (3) to dithiocarbonylation to obtain the compound of the above-mentioned general formula (5), subjecting the compound of the general formula (5) to radical reduction to obtain the inosine derivative represented by the above-mentioned general formula (1), and eliminating the substituents R1 from the inosine derivative represented by the general formula (1).

The present invention provides a method for producing DDI comprising the step of hydrogenating 2',3'-didehydro-2',3'-dideoxyinosine (D4I) obtained by the above-mentioned methods, and 2',3'-dideoxyinosine (DDI) obtainable by the above-mentioned production method.

Furthermore, the present invention provides inosine derivatives represented by the following general formula (1):

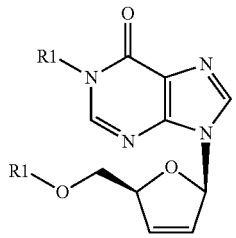

(1)

wherein R1 may be the same or different and are each benzyl group, benzhydryl group or trityl group, each of which may have a substituent.

The present invention also provides inosine derivatives represented by the following general formula (2).

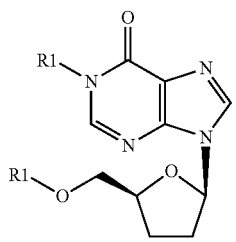

(2)

The present invention also provides inosine derivatives represented by the following general formula (5).

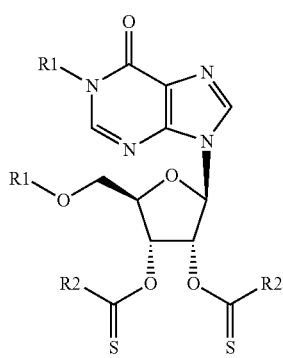

(5)

The present invention also provides inosine derivatives represented by the following general formula (6).

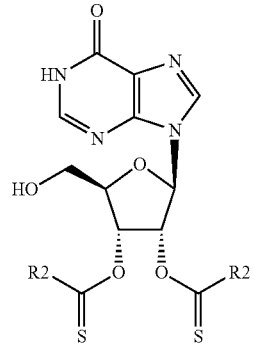

(6)

In general formulas (2), (5) and (6), R1 and R2 are the same as those previously defined.

BEST MODE FOR CARRYING OUT THE INVENTION

In the aforementioned general formulas (1) through (3) and (5), R1 may be the same or different and are each benzyl group, benzhydryl group or trityl group, each of which may have a substituent. In particular, benzyl group which may have a substituent is preferable from the viewpoints of yield and economical efficiency. In the case where R1 has a substituent, the position and the number of substituents are not particularly limited. Examples of the substituents for R1 include an alkyl group having 1 to 12 carbon atoms such as methyl group, ethyl group, n-propyl group, i-propyl group, n-butyl group, i-butyl group, sec-butyl group, tert-butyl group or the like; a cycloalkyl groups having 3 to 12 carbon atoms such as cyclopropyl group, cyclobutyl group, cyclopentyl group, cyclohexyl group or the like; an alkoxyl group having 1 to 12 carbon atoms such as methoxy group, ethoxy group, n-propoxy group, i-propoxy group, n-butoxy group, tert-butoxy group or the like; an acyloxy group having 2 to 12 carbon atoms such as acetoxy group, benzoyloxy group or the like; hydroxyl group; a halogen atom such as fluorine, chlorine, bromine, iodine or the like; vinyl group; allyl group; an aryl group such as phenyl group, naphthyl group, furyl group, indolyl group, pyridyl group or the like; a carbonyl group such as formyl group, acetyl group, trifluoroacetyl group, benzoyl group, methoxycarbonyl group, ethoxycarbonyl group, tert-butoxycarbonyl group, vinyloxycarbonyl group, allyloxycarbonyl group, benzyloxycarbonyl group, methylaminocarbonyl group or the like; a sulfonyl group such as alkylsulfonyl group, arylsulfonyl group, sulfonamide or the like; amino group; a primary amino group such as N-methylamino group, N-ethylamino group, N-n-propylamino group, N-isopropylamino group, N-n-butylamino group, N-isobutylamino group, N-tert-butylamino group, N-benzylamino group, N-methoxycarbonylamino group, N-tert-butoxycarbonylamino group, N-phenylamino group, N-mesylamino group, N-tosylamino group, N-formylamino group or the like; a secondary amino group such as N,N-dimethylamino group, N,N-diethylamino group, N,N-dibenzylamino group, N-ethyl-N-methylamino group, N,N-di-n-propylamino group, N,N-diisopropylamino group, N,N-diphenylamino group, N-methyl-N-phenylamino group, N-methyl-N-benzylamino group, N-mesyl-N-methylamino group, piperidyl group, pyrrolidyl group or the like; nitro group; nitroso group; cyano group; and a haloalkyl group such as monofluoromethyl group, difluoromethyl group, trifluoromethyl group, monochloromethyl group, dichloromethyl group, trichloromethyl group, pentafluoroethyl group or the like. The alkoxyl group having 1 to 12 carbon atoms is preferable as the substituent for R1. As the group represented by R1, particularly preferable are unsubstituted benzyl group and benzyl group having as a substituent an alkoxyl group with 1 to 12 carbon atoms, preferably methoxy group, more preferably methoxy group at the para-position.

The inosine derivative represented by the above-mentioned general formula (1) can be produced, for example, by (i) subjecting the inosine derivative represented by the above-mentioned general formula (3) to dithiocarbonylation to obtain the thiocarbonylated inosine derivative of the above-mentioned general formula (5), and (ii) carrying out the radical reduction of the obtained compound of general formula (5).

The inosine derivative represented by the above-mentioned general formula (3) can be prepared, for example, by a conventional method described in the literature: Luzzio, F. A. et al. J. Org. Chem., 1994, 59, 7267-7272. More specifically, hydroxyl groups at the 2'- and 3'-positions of inosine are protected by ketal, and thereafter benzyl group or the like is introduced into the obtained compound to achieve deprotection of the ketal, so that the inosine derivative of general formula (3) can be produced. The amounts of raw materials, proper reaction conditions, the kind and the amount of solvent, the catalyst and the like are known to those skilled in the art.

In the above-mentioned formulas (5) and (6), R2 may be the same or different, and are each an alkylthio group having 1 to 12 carbon atoms, an alkoxyl group having 1 to 12 carbon atoms, or an alkylamino group having 1 to 12 carbon atoms. Each of those groups may have a substituent. In consideration of the yield and economical efficiency, an alkylthio group having 1 to 12 carbon atoms which may have a substituent is preferable. In the case where R2 has a substituent, the position and the number of substituents are not particularly limited. Examples of the substituents for R2 include an alkoxyl group having 1 to 12 carbon atoms such as methoxy group, ethoxy group, n-propoxy group, i-propoxy group, n-butoxy group, tert-butoxy group or the like; hydroxyl group; a halogen atom such as fluorine, chlorine, bromine, iodine or the like; a heteroaryl group such as furyl group, indolyl group, pyridyl group or the like; a sulfonyl group such as alkylsulfonyl group, arylsulfonyl group, sulfonamide or the like; amino group; a primary amino group such as N-methylamino group, N-ethylamino group, N-n-propylamino group, N-isopropylamino group, N-n-butylamino group, N-isobutylamino group, N-tert-butylamino group, N-benzylamino group, N-phenylamino group, N-mesylamino group, N-tosylamino group or the like; a secondary amino group such as N,N-dimethylamino group, N,N-diethylamino group, N,N-dibenzylamino group, N-ethyl-N-methylamino group, N,N-di-n-propylamino group, N,N-diisopropylamino group, N,N-diphenylamino group, N-methyl-N-phenylamino group, N-methyl-N-benzylamino group, N-mesyl-N-methylamino group, piperidyl group, pyrrolidyl group or the like; nitro group; nitroso group; cyano group, and so on. Particularly, cyano group is preferable as the substituent for R2. As the group represented by R2, methylthio group, and ethylthio group and 2-cyanoethylthio group are preferable, and methylthio group is more preferable.

(i) In the present invention, the inosine derivative of general formula (3) is first subjected to dithiocarbonylation to obtain the thiocarbonylated inosine derivative represented by general formula (5). To achieve the step of dithiocarbonylation, the processes for thiocarbonylation, such as alkylthio-thiocarbonylation, alkoxy-thiocarbonylation, alkylamino-thiocarbonylation and the like can be employed.

The process of alkylthio-thiocarbonylation can be carried out by allowing the inosine derivative of general formula (3) to react with carbon disulfide and an alkyl halide in the presence of a base in an appropriate solvent. Examples of the solvent include dimethyl sulfoxide (DMSO), dimethylformamide (DMF), N-methylpyrrolidone, tetrahydrofuran and the like. In particular, DMSO is preferable. The amount of solvent may be preferably in the range of 0.5 to 5 L, more preferably 1 to 2 L, with respect to 1 mol of the inosine derivative of general formula (3). It is preferable that the amount of carbon disulfide be 2 to 4 equivalent weights, more preferably 2 to 2.5 equivalent weights, with respect to the inosine derivative of general formula (3). The base includes sodium hydroxide, potassium hydroxide, sodium carbonate, potassium carbonate, sodium hydride and the like, and sodium hydroxide and potassium hydroxide are preferably used. The amount of base may be preferably 2 to 4 equivalent weights, more preferably 2 to 2.5 equivalent weights, with respect to the inosine derivative of general formula (3). Examples of the alkyl halide to be used include methyl iodide, ethyl iodide, 2-cyanoethyl bromide and the like. In particular, methyl iodide and 2-cyanoethyl bromide are preferable. The amount of alkyl halide is preferably 2 to 5 equivalent weights, more preferably 2 to 3 equivalent weights, with respect to the inosine derivative of general formula (3). The reaction temperature, which varies depending upon the kind of solvent, is generally in the range of −20 to 50° C., preferably 0 to 30° C. It is preferable to carry out the reaction within the above-mentioned temperature range from the viewpoint of yield. The reaction time is generally in the range of 0.1 to 10 hours, preferably 1 to 3 hours. To cause the reaction within the above-mentioned time range produces good results in terms of yield.

The process of alkoxy-thiocarbonylation can be carried out, for example, as described in WO0173095, by allowing the inosine derivative of general formula (3) to react with an alkoxy-thiocarbonyl halide in the presence of a base in an appropriate solvent. Examples of the solvent include organic solvents such as acetonitrile, dimethylformamide (DMF), pyridine, ethyl acetate, toluene and the like. Acetonitrile is preferable. The amount of solvent may be preferably in the range of 0.5 to 5 L, more preferably 1 to 2 L, with respect to 1 mol of the inosine derivative of general formula (3). The base includes organic tertiary amines such as pyridine, triethylamine, N-ethylpiperidine, N-ethylmorpholine and the like, and triethylamine and pyridine are preferably used. The amount of base is preferably 2 to 4 equivalent weights, more preferably 2 to 2.5 equivalent weights, with respect to the inosine derivative of general formula (3). The reaction temperature, which varies depending upon the kind of solvent, is generally in the range of −50 to 50° C., preferably −20 to 20° C. It is preferable to carry out the reaction within the above-mentioned temperature range from the viewpoint of yield. The reaction time is generally in the range of 0.1 to 5 hours, preferably 0.5 to 2 hours. To cause the reaction within the above-mentioned time range produces good results in terms of yield.

The process of alkylamino-thiocarbonylation can be carried out by a method as described in, for example, Nishiyama, K. et al. Tetrahedron Lett., 2003, 44, 4027-4029, Izawa, K. et al. Tetrahedron Lett., 2001, 42, 7605-7608, or the like. More specifically, the inosine derivative of general formula (3) may be allowed to react with phenyl isothiocyanate or 1,1'-thiocarbonyl diimidazole in an appropriate solvent, in the presence of a base when necessary. Examples of the solvent include organic solvents such as dimethylformamide (DMF), tetrahydrofuran, acetonitrile and the like. In particular, dimethylformamide and tetrahydrofuran are preferable. The amount of solvent may be preferably in the range of 0.5 to 5 L, more preferably 1 to 2 L, with respect to 1 mol of the inosine derivative of general formula (3). The base includes sodium hydride, sodium hydroxide, potassium hydroxide and the like, and sodium hydride is preferably used. The amount of base is preferably 2 to 4 equivalent weights, more preferably 2 to 2.5 equivalent weights, with respect to the inosine derivative of general formula (3). The reaction may proceed in the absence of a base, and therefore the base is not always necessary. The reaction temperature, which varies depending upon the kind of solvent, is generally in the range of −20 to 100° C., preferably 0 to 80° C. It is preferable to carry out the reaction within the above-mentioned temperature range from the viewpoint of yield. The reaction time is generally in the range of 0.1 to 5 hours, preferably 0.5 to 2 hours. To cause the reaction within the above-mentioned time range produces good results in terms of yield.

(ii) According to the present invention, the compound of general formula (1) can be obtained by subjecting the compound represented by general formula (5) to radical reduction.

Examples of the solvent that can be used in this step include dimethoxyethane (DME), acetonitrile, acetic ester, 1,4-dioxane, tetrahydrofuran (THF), and alcohols such as methanol, ethanol, 2-propanol and the like. In particular, acetonitrile, 1,4-dioxane and tetrahydrofuran (THF) are preferable. The amount of solvent may be preferably in the range of 0.5 to 5 L, more preferably 1 to 2 L, with respect to 1 mol of the compound represented by general formula (5).

A radical reducing agent that can be used in this step includes hypophosphorous acid and salts thereof, for example, N-ethylpiperidine hypophosphite, tributyl tin hydride, silane compounds such as diphenyl silane, and the like. In particular, hypophosphorous acid and salts thereof are preferable, and N-ethylpiperidine hypophosphite is particularly preferable. The amount of radical reducing agent is generally 1 to 20 equivalent weights, preferably 1 to 5 equivalent weights, with respect to 1 mol of the compound obtained in the step (i).

A radical initiator that can be used in this step includes azobisisobutyronitrile (AIBN), triethylborane, and the like. In particular, AIBN is preferable. The amount of radical initiator is generally 0.01 to 2 equivalent weights, preferably 0.1 to one equivalent weight, with respect to 1 mol of the compound represented by general formula (5).

The reaction temperature for this step, which varies depending upon the kind of solvent, is preferably in the range of 0 to 120° C., more preferably 20 to 90° C. It is preferable to carry out the reaction within the above-mentioned temperature range from the viewpoint of yield.

In this step, the reaction time is typically in the range of 0.1 to 10 hours, preferably 1 to 5 hours. To cause the reaction within the above-mentioned time range produces good results in terms of yield.

After the completion of the above-mentioned reaction in the present invention, the obtained product may be further purified by chromatography or the like.

(iii) According to the present invention, the compound represented by the aforementioned general formula (2) can be produced by, for example, hydrogenating the compound represented by the aforementioned general formula (1).

A catalyst that can be used in the present invention includes palladium-carbon, palladium hydroxide-carbon, platinum-carbon and the like. In particular, palladium-carbon and palladium hydroxide-carbon are preferable.

The atmospheric pressure of hydrogen is preferably in the range of 0.5 to 10 atmospheres, more preferably 0.8 to 2 atmospheres.

Any organic solvents can freely be used for the solvent for use in the present invention. DMF, methanol, ethanol, acetonitrile and tetrahydrofuran are preferable, and methanol is particularly preferable.

The reaction temperature in the present invention, which varies depending upon the kind of solvent, is preferably in the range of 10 to 60° C., more preferably 20 to 50° C.

In this, step, the reaction time is typically in the range of 0.1 to 10 hours, preferably 1 to 5 hours.

After the completion of the above-mentioned reaction in the present invention, the obtained product may be further purified by chromatography or the like.

(iv) In the present invention, the intended DDI (7) can be derived from the inosine derivative represented by the above-mentioned general formula (1) or (2) through hydrogenation. To be more specific, a double bond in a sugar moiety of the inosine derivative represented by the above-mentioned general formula (1) is subjected to hydrogenation, so as to derive the inosine derivative represented by the above-mentioned general formula (2). Further, the protective groups R1 are eliminated by hydrogenolysis, thereby leading to the intended DDI. In this case, according to a preferred embodiment, a double bond in a sugar moiety of the inosine derivative represented by the above-mentioned general formula (1) is subjected to hydrogenation in the presence of a metal catalyst in an atmosphere of hydrogen so as to derive the inosine derivative represented by the above-mentioned general formula (2). Subsequently, a first benzyl group is eliminated in the presence of an alkali at room temperature, and thereafter a second benzyl group is eliminated by the reaction where the pressure of hydrogen is increased and/or the temperature is raised, thereby converting the inosine derivative of general formula (2) into the desired DDI. According to a particularly preferable embodiment in this case, sodium hydroxide or potassium hydroxide is used as an alkali, and the reaction time for elimination of the first benzyl group is in the range of 0.5 to 5 hours. The second benzyl group is eliminated under the conditions that the pressure of hydrogen is preferably set to 0.5 to 10 atmospheres, more preferably 0.8 to 2 atmospheres, the temperature is set to 40 to 150° C., preferably 60 to 120° C., and the reaction time is set to 2 to 24 hours.

(v) From the compound of aforementioned general formula (1), D4I (4) can also be obtained by subsequent elimination of the substituents represented by R1. This process is particularly useful in the case where the inosine derivative of general formula (3) is used as a starting material where R1 is benzyl group having an alkoxyl group with 1 to 12 carbon atoms, preferably methoxy group, more preferably methoxy group at the para-position.

As an agent for eliminating the substituents R1 (i.e., deprotecting agent) that can be used in this step, diammonium cerium (IV) nitrate, 2,3-dichloro-5,6-dicyano-1,4-benzoquinone and the like can be employed. In particular, diammonium cerium (IV) nitrate and 2,3-dichloro-5,6-dicyano-1,4-benzoquinone are preferable. The amount of this agent is preferably in the range of 1 to 5 mol, more preferably 2 to 3 mol, with respect to 1 mol of the compound of general formula (1).

Examples of the solvent that can be used in this step include a mixed solvent of acetonitrile and water, a mixed solvent of dichloromethane and water, tetrahydrofuran, and so on. In particular, a mixed solvent of acetonitrile and water is preferable. The amount of solvent is preferably in the range of 1 to 100 mL, more preferably 10 to 50 mL, with respect to 1 mol of the compound having general formula (1).

The reaction temperature for this step, which varies depending upon the kind of solvent, is preferably in the range of 0 to 100° C., more preferably room temperature. It is preferable to carry out the reaction within the above-mentioned temperature range from the viewpoint of yield. The reaction time for this step is typically in the range of 0.1 to 10 hours, preferably 2 to 5 hours. To cause the reaction within the above-mentioned time range produces good results in terms of yield. This step can preferably give the D4I (4) in high yields.

After the completion of the reaction in this step, the obtained product may be further purified by chromatography or the like.

(vi) In the present invention, a thiocarbonyl inosine represented by general formula (6) is obtained by eliminating the substituents R1 from the compound of general formula (5). This process is particularly useful in the case where the inosine derivative of general formula (3) is used as a starting material where R1 is benzyl group having an alkoxyl group with 1 to 12 carbon atoms, preferably, methoxy group, more preferably, methoxy group at the para-position.

The same agent for eliminating the substituents R1 as used in the step (v) can be used in this step. In particular, diammonium cerium (IV) nitrate and 2,3-dichloro-5,6-dicyano-1,4-benzoquinone are preferable. The amount of this agent is preferably in the range of 1 to 5 mol, more preferably 2 to 3 mol, with respect to 1 mol of the compound having general formula (5).

The solvent that can be used in this step and the amount thereof, the reaction temperature, and the reaction time are the same as those described in the conditions of the step (iv), and the preferable conditions and the reasons therefor described in the step (iv) are also applied to this case.

After the completion of the reaction in this step, the obtained product may be further purified by chromatography or the like.

(vii) In the present invention, D4I (4) can be obtained by subjecting the compound represented by general formula (6) to radical reduction.

The same radical reducing agents that can be used in the step (ii) are applicable to this step. In particular, hypophosphorous acid and salts thereof are preferable, and N-ethylpiperidine hypophosphite is more preferable. The amount of radical reducing agent is preferably 1 to 20 equivalent weights, more preferably 1 to 5 equivalent weights, with respect to 1 mol of the compound of general formula (6).

Examples of the solvent that can be used in this step include a mixed solvent of tetrahydrofuran and triethylborane hexane solution, acetonitrile, 1,4-dioxane, tetrahydrofuran (THF) and the like. In particular, a mixed solvent of tetrahydrofuran and triethylborane hexane solution is preferable. The amount of solvent is preferably in the range of 0.5 to 5 L, more preferably 1 to 2 L, with respect to 1 mol of the compound of general formula (6).

The reaction temperature for this step, which varies depending upon the kind of solvent, is preferably in the range of 0 to 120° C., more preferably, room temperature. It is preferable to carry out the reaction within the above-mentioned temperature range from the viewpoint of yield. In this step, the reaction time is typically in the range of 0.1 to 10 hours, preferably 1 to 50 hours. To cause the reaction within the above-mentioned time range produces good results in terms of yield. This step can preferably give the D4I in high yields.

After the completion of the reaction in this step, the obtained product may be further purified by chromatography or the like.

(viii) In the present invention, DDI (7) can also be obtained by subjecting the D4I (4) prepared through the step (vii) to hydrogenation, using the technique known in the art (refer to, for example, Chu, C. K. et al. J. Org. Chem. 1989, 54, 2217-2225).

The catalyst that can be used in this step and the amount thereof, the solvent that can be used in this step and the amount thereof, the reaction temperature, and the reaction time are the same as those described in the conditions of the step and the preferable conditions and the reasons therefor described in the step (iii) are also applied to this case.

The D4I (4) or the inosine derivative represented by general formula (2) can be produced by following the sequence of the steps combined as shown below: (i)-(ii)-(iii), (i)-(ii)-(v), or (i)-(vi)-(vii). In particular, the D4I can preferably be obtained in remarkably high yields by following the steps of (i), (vi) and (vii) in this order, using as the raw material an inosine derivative of general formula (3) where R1 is p-methoxybenzyl group.

After the D4I or the inosine derivative represented by general formula (2) is obtained by any of the aforementioned combinations of the steps, the additional step (iv) or (viii) can provide the DDI (7). Namely, the DDI can be produced by following the sequence of the steps combined as shown below: (i)-(ii)-(iii)-(iv), (i)-(i)-(v)-(viii), or (i)-(vi)-(vii). In particular, the DDI can preferably be obtained in remarkably high yields by following the steps of (i), (vi), (vii) and (viii) in this order, using as the raw material an inosine derivative of general formula (3) where R1 is p-methoxybenzyl group.

After the completion of the reactions in the present invention, the obtained product may further be purified by conventional processes, such as chromatography, crystallization and the like to obtain a targeted DDI.

The present invention will now be explained in detail with reference to the following Examples.

EXAMPLES

Example 1

Synthesis of dibenzyl-2',3'-bis-O—[(methylthio)thiocarbonyl]inosine

To a dimethyl sulfoxide solution (1 mL) of $N^1$,5'-O-dibenzyl inosine (224 mg, 0.5 mmol) synthesized in accordance with a method described in Luzzio, F. A. et al. J. Org. Chem., 1994, 59, 7267-7272, an aqueous solution of sodium hydroxide (0.28 mL, 1.1 mmol) at a concentration of 4.0 mol/L and carbon disulfide (0.09 mL, 1.5 mmol) were added, and the obtained mixture was stirred at room temperature for 2 hours. To the obtained solution, methyl iodide (0.07 mL, 1.1 mmol) was added dropwise, the mixture was then stirred at room temperature for one hour. Then, with the addition of ethyl acetate (10 mL) and water (2 mL), the reaction was terminated. After the layers were separated, the resultant water layer was again extracted by the addition of ethyl acetate (10 mL). The two organic layers thus obtained were combined and dried over anhydrous magnesium sulfate, and then concentrated under reduced pressure. After purification by chromatography (using 15 g of silica gel and a mixed solvent of hexane and ethyl acetate (1:2) as an eluting solution), 276 mg of the intended product was obtained in a yield of 88% as a colorless oily material.

$^1$H-NMR (CDCl$_3$): δ 2.53 (s, 3H), δ 2.60 (s, 3H), δ 3.75-3.90 (m, 2H), δ 4.58 (m, 1H), δ 4.63 (s, 2H), δ 5.25 (s, 1H), δ 6.44 (m, 2H), δ 6.62 (m, 1H), δ 7.25-7.39 (m, 10H), δ 7.96 (s, 1H), δ 8.01 (s, 1H). $^{13}$C-NMR (CDCl$_3$): δ 19.79, 19.88, 49.58, 69.68, 74.30, 79.55, 80.87, 83.56, 85.60, 125.11, 128.05, 128.35, 128.55, 128.71, 129.03, 129.41, 136.35, 137.40, 138.76, 147.81, 148.02, 156.84, 214.71, 215.05. ESIMS m/z 629 (M+H).

Example 2

Synthesis of N$^1$,5'-O-dibenzyl-2',3'-didehydro-2',3'-dideoxyinosine

An acetonitrile solution (1 mL) of N$^1$,5'-O-dibenzyl-2',3'-bis-O-[(methylthio)thiocarbonyl]inosine (314 mg, 0.5 mmol) was heated to 80° C. To this solution, an acetonitrile solution (1 mL) of N-ethylpiperidine hypophosphite (358 mg, 2 mmol) and 2,2'-azobisisobutyronitrile (16.4 mg, 0.1 mmol) were added, and the mixture was then stirred at 90° C. for one hour. After the reaction mixture was cooled, the reaction was terminated with the addition of water (3 mL). The reaction mixture was extracted by the addition of ethyl acetate (15 mL), and the resultant organic layer was dried over anhydrous magnesium sulfate and concentrated under reduced pressure. After purification by chromatography (using 12 g of silica gel and a mixed solvent of hexane and ethyl acetate (1:2) as an eluting solution), 150 mg of the intended product was obtained in a yield of 71% as a colorless oily material.

$^1$H-NMR (CDCl$_3$): δ 3.61 (d, 2H, J=3.8 Hz), δ 4.45 (d, 1H, J=12.2 Hz), δ 4.54 (d, 1H, J=12.2 Hz), δ 5.06 (m, 1H), δ 5.25 (d, 1H, J=14.7 Hz), δ 5.31 (d, 1H, J=14.7 Hz), δ 6.01 (d, 1H, J=6.0 Hz), δ 6.40 (d, 1H, J=6.0 Hz), δ 6.98 (s, 1H), δ 7.21-7.37 (m, 10H), δ 8.00 (s, 1H), δ 8.03 (s, 1H). $^{13}$C-NMR (CDCl$_3$): δ 49.47, 71.13, 73.82, 86.89, 88.54, 124.80, 125.38, 128.27, 128.48, 128.62, 128.71, 128.87, 129.36, 135.02, 136.56, 137.82, 139.24, 147.65, 147.69, 157.04. ESIMS m/z: 417 (M+H).

Example 3

Synthesis of N$^1$,5'-O-dibenzyl-2',3'-dideoxyinosine

To a methanol solution (1 mL) of N$^1$,5'-O-dibenzyl-2',3'-didehydro-2',3'-dideoxyinosine (207 mg, 0.5 mmol), 5% palladium-carbon (20 mg) was added, and the mixture was stirred at room temperature for 2 hours in an atmosphere of hydrogen (1 atm). The palladium catalyst was removed from the obtained reaction mixture by filtration, and the resultant filtrate was concentrated under reduced pressure. After purification by chromatography (using 15 g of silica gel and ethyl acetate as an eluting solution), 187 mg of the intended product was obtained in a yield of 90% as a white solid.

$^1$H-NMR (CDCl$_3$): δ 2.08-2.17 (m, 2H), δ 2.40-2.49 (m, 2H), δ 3.59 (d-d, 1H, J=10.5, 4.4 Hz), δ 3.73 (d-d, 1H, J=10.5, 3.3 Hz), δ 4.30-4.40 (m, 1H), δ 4.55 (d, 1H, J=12.2 Hz), δ 4.60 (d, 1H, J=12.2 Hz), δ 5.24 (d, 1H, J=14.7 Hz), δ 5.28 (d, 1H, J=14.7 Hz), δ 6.24 (d-d, 1H, J=6.5, 3.3 Hz), δ 7.27-7.37 (m, 10H), δ 7.97 (s, 1H), δ 8.14 (s, 1H). $^{13}$C-NMR (CDCl$_3$): δ 26.43, 33.58, 49.43, 71.48, 73.90, 81.20, 85.78, 125.29, 128.20, 128.26, 128.41, 128.52, 128.91, 129.38, 136.55, 138.05, 138.83, 147.08, 147.16, 157.04. ESIMS m/z: 415 (M+H).

Example 4

Synthesis of 2',3'-dideoxyinosine (DDI)

To a N,N-dimethylformamide solution (1 mL) of N$^1$,5'-O-dibenzyl-2',3'-dideoxyinosine (52 mg, 0.125 mmol), an aqueous solution of sodium hydroxide (0.3 mL) at a concentration of 1 mol/L was added, and the mixture was stirred at room temperature for 2 hours. To the obtained solution, 20% palladium hydroxide-carbon (10 mg) was added, and the mixture was stirred at room temperature for 2 hours in an atmosphere of hydrogen (1 atm) and thereafter stirred at 80° C. for 16 hours and at 100° C. for 6 hours. The palladium catalyst was removed from the obtained reaction mixture by filtration, and the resultant filtrate was concentrated under reduced pressure. After purification by chromatography (using 10 g of silica gel and a mixed solvent of dichloromethane and methanol (4:1) as an eluting solution), 21 mg of the intended product was obtained in a yield of 70% as a white solid.

$^1$H-NMR (DMSO-d$_6$): δ 2.00-2.07 (m, 2H), δ 2.31-2.53 (m, 2H), δ 3.52 (m, 1H), δ 3.62 (m, 1H), δ 4.11 (m, 1H), δ 4.96 (m, 1H), δ 6.21 (d-d, 1H, J=6.8, 3.3 Hz), δ 8.05 (s, 1H), δ 8.33 (s, 1H). $^{13}$C-NMR (DMSO-d$_6$): δ 25.77, 32.49, 62.96, 82.40, 84.80, 124.64, 138.54, 145.97, 147.94, 156.98. ESIMS m/z: 237 (M+H).

Example 5

Synthesis of N$^1$, 5'-O-di-p-methoxybenzyl-2',3'-bis-O-[(methylthio)thiocarbonyl]inosine To a N,N-dimethylformamide solution (5 mL) of N$^1$,5'-O-di-p-methoxybenzyl inosine (400 mg, 0.78 mmol) synthesized in accordance with a method described in Luzzio, F. A. et al. J. Org. Chem., 1994, 59, 7267-7272, a 60% mineral oil dispersion of sodium hydride (94 mg, 2.34 mmol) was added and the obtained mixture was stirred at room temperature for 2 hours, and thereafter carbon disulfide (0.48 mL, 7.88 mmol) was added thereto and the obtained mixture was stirred at room temperature for 12 hours. With the addition of methyl iodide (0.5 mL, 7.88 mmol), the obtained solution was stirred at room temperature for 3 hours. Then, the reaction mixture was concentrated under reduced pressure and diluted with ethyl acetate. The resultant organic layer was washed with water, and thereafter dried over anhydrous magnesium sulfate and concentrated under reduced pressure. After purification by chromatography (using as eluting solutions a mixed solvent of hexane and ethyl acetate (1:1), a mixed solvent of hexane and ethyl acetate (3:7), and ethyl acetate successively in this order), 484 mg of the intended product was obtained in a yield of 82%. $^1$H NMR (CDCl$_3$): δ 2.50 (s, 6H), δ 2.89 (s, 2H), δ 2.96 (s, 2H), δ 3.80 (s, 6H), δ 4.69-4.87 (m, 3H), δ 5.71-5.81 (m, 1H), δ 6.13 (m, 1H), δ 6.29 (m, 1H), δ 6.84-6.92 (m, 4H), δ 7.15-7.36 (m, 4H), δ 7.88 (s, 1H), δ 8.04 (s, 1H).

Example 6

Synthesis of $N^1$,5'-O-di-p-methoxybenzyl-2°,3'-didehydro-2',3'-dideoxyinosine

To a 1,4-dioxane solution of N-ethylpiperidine hypophosphite (2.04 mL, 3.6 mmol) at a concentration of 1.764 mol/L, a mixed solution of a tetrahydrofuran solution (3 mL) containing $N^1$, 5'-O-di-p-methoxybenzyl-2',3'-bis-O-[(methylthio) thiocarbonyl]inosine (250 mg, 0.36 mmol) and a triethylborane hexane solution (0.36 mL, 0.36 mmol) at a concentration of 1.0 mol/L was added, and the obtained mixture was stirred at room temperature for one hour. The obtained reaction mixture was diluted with ethyl acetate. The resultant organic layer was washed with brine solution, and thereafter dried over anhydrous magnesium sulfate and concentrated under reduced pressure. After purification by chromatography (using as eluting solutions a mixed solvent of hexane and ethyl acetate (3:7), ethyl acetate, and a mixed solvent of dichloromethane and methanol (10:1) successively in this order), 169 mg of the intended product was obtained in a yield of 98%. $^1$H NMR (CDCl$_3$): δ 2.89 (s, 2H), δ 2.97 (s, 2H), δ 3.79 (s, 6H), δ 3.9 (m, 2H), δ 4.51 (m, 1H), δ 4.87 (m, 1H), δ 5.95 (m, 1H), δ 6.81 (m, 1H) δ 6.78-6.90 (m, 4H), δ 7.10-7.39 (m, 4H), δ 7.99 (s, 1H), δ 8.01 (s, 1H).

Example 7

Synthesis of 2',3'-didehydro-2',3'-dideoxyinosine (D4I)

To an acetonitrile-water mixed (3:1) solution (5 mL) containing $N^1$,5'-O-di-p-methoxybenzyl-2',3'-didehydro-2',3'-dideoxyinosine (150 mg, 0.32 mmol), diammonium cerium (IV) nitrate (526 mg, 0.96 mmol) was added, and the obtained mixture was stirred at room temperature for 3 hours. The obtained reaction mixture was diluted with ethyl acetate. The resultant organic layer was washed with brine solution, and thereafter dried over anhydrous magnesium sulfate and concentrated under reduced pressure, whereby 75 mg of the intended product was obtained in a yield of 99%. $^1$H NMR (DMSO-d$_6$): δ 3.57 (m, 2H), δ 4.89 (m, 1H), δ 6.14 (m, 1H), δ 6.48 (m, 1H), δ 6.91 (m, 1H), δ 8.08 (s, 1H), δ 8.11 (s, 1H).

Example 8

Synthesis of 2',3'-bis-O-[(methylthio)thiocarbonyl]inosine

To an acetonitrile-water mixed (3:1) solution (4 mL) containing $N^1$,5'-O-di-p-methoxybenzyl-2',3'-bis-O-[(methylthio)thiocarbonyl]inosine (151 mg, 0.22 mmol), diammonium cerium (IV) nitrate (362 mg, 0.66 mmol) was added, and the obtained mixture was stirred at room temperature for 3 hours. The obtained reaction mixture was diluted with ethyl acetate. The resultant organic layer was washed with brine solution, and thereafter dried over anhydrous magnesium sulfate and concentrated under reduced pressure, whereby 99 mg of the intended product was obtained in a yield of 99%. $^1$H NMR (DMSO-d$_6$): δ 2.50 (s, 6H), δ 3.59 (m, 2H), δ 4.95 (m, 1H), δ 5.18 (m, 1H) δ 6.11 (m, 1H), δ 6.25 (m, 1H), δ 7.89 (s, 1H), δ 8.04 (s, 1H).

Example 9

Synthesis of 2',3'-bis-O-[(methylthio)thiocarbonyl]inosine

To a dichloromethane-water mixed (18:1) solution (7.2 mL) containing $N^1$,5'-O-di-p-methoxybenzyl-2',3'-bis-O-[(methylthio)thiocarbonyl]inosine (151 mg, 0.22 mmol), 2,3-dichloro-5,6-dicyano-1,4-benzoquinone (150 mg, 0.66 mmol) was added, and the obtained mixture was stirred at room temperature for 3 hours. The obtained reaction mixture was diluted with ethyl acetate. The resultant organic layer was washed with brine solution, and thereafter dried over anhydrous magnesium sulfate and concentrated under reduced pressure.

After purification by chromatography (using as eluting solutions mixed solvents of hexane and ethyl acetate at concentrations of 1:1, 3:7, and 2:8 successively in this order), 87 mg of the intended product was obtained in a yield of 88%.

Example 10

Synthesis of 2',3'-bis-O-[(methylthio)thiocarbonyl]inosine

To a tetrahydrofuran solution (10 mL) containing $N^1$,5'-O-di-p-methoxybenzyl-2',3'-bis-O—[(methylthio)thiocarbonyl]inosine (151 mg, 0.22 mmol), 10% palladium-carbon (23 mg) was added, and the obtained mixture was stirred at room temperature for 2 days in an atmosphere of hydrogen (1 atm). The palladium catalyst was removed from the obtained reaction mixture by filtration, and the resultant filtrate was concentrated under reduced pressure. After purification by chromatography (using as eluting solutions mixed solvents of hexane and ethyl acetate at concentrations of 1:1, 3:7, and 2:8 successively in this order), 42 mg of the intended product was obtained in a yield of 43%

Example 11

Synthesis of 2',3'-didehydro-2',3'-dideoxyinosine (D4I)

To a 1,4-dioxane solution containing N-ethylpiperidine hypophosphite (1.25 mL, 2.2 mmol) at a concentration of 1.764 mol/L, a mixed solution of a tetrahydrofuran solution (2 mL) of 2',3'-bis-O-[(methylthio)thiocarbonyl]inosine (99 mg, 0.22 mmol) and a triethylborane hexane solution (0.22 mL, 0.22 mmol) at a concentration of 1.0 mol/L was added, and the obtained mixture was stirred at room temperature for one hour. The obtained reaction mixture was diluted with ethyl acetate. The resultant organic layer was washed with brine solution, and thereafter dried over anhydrous magnesium sulfate and concentrated under reduced pressure. After purification by chromatography (using as eluting solutions a mixed solvent of hexane and ethyl acetate (3:7), ethyl acetate, and a mixed solvent of dichloromethane and methanol (10:1) successively in this order), 47 mg of the intended product was obtained in a yield of 92%.

According to the production methods of the present invention, DDI can inexpensively be synthesized in satisfactory yields through the curtailed steps. As a result, the value of the present invention can be enhanced because the production of compounds useful as the anti-AIDS drugs can be achieved on industrial scale.

The invention claimed is:

1. A method for producing an inosine compound represented by formula (1):

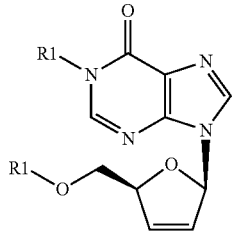

(1)

wherein each R1 may be the same or different and each is a benzyl group, a benzhydryl group, or a trityl group, each of which may have a substituent,
said method comprising:
subjecting an inosine compound represented by formula (3):

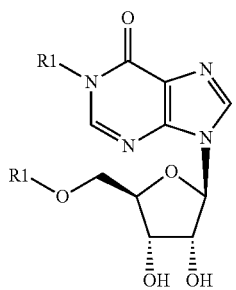

(3)

wherein each R1 is as defined above,
to dithiocarbonylation to obtain a compound; and
radically reducing said obtained compound, to obtain said inosine compound represented by formula (1).

2. A method according to claim 1, wherein each R1 in formulae (1) and (3) is a benzyl group which may have a substituent.

3. A method according to claim 1, wherein each R1 in formulae (1) and (3) is independently a benzyl group having as a substituent an alkoxyl group with 1 to 12 carbon atoms or an unsubstituted benzyl group.

4. A method for producing an inosine compound represented by formula (2):

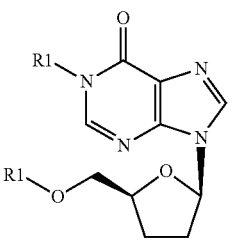

(2)

wherein each R1 may be the same or different and each is a benzyl group, a benzhydryl group or a trityl group, each of which may have a substituent,
said method comprising:
hydrogenating an inosine compound represented by formula (1):

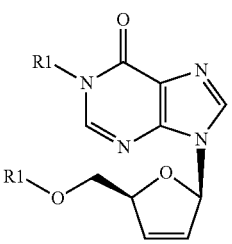

(1)

wherein each R1 is as defined above,
to obtain said inosine compound represented by formula (2).

5. A method according to claim 4, wherein each R1 in formulae (1) and (2) is a benzyl group which may have a substituent.

6. A method according to claim 4, wherein each R1 in formulae (1) and (2) is independently a benzyl group having as a substituent an alkoxyl group with 1 to 12 carbon atoms or an unsubstituted benzyl group.

* * * * *